(12) United States Patent
Bourne

(10) Patent No.: US 7,951,136 B2
(45) Date of Patent: May 31, 2011

(54) COUPLER WRENCH

(75) Inventor: John M. Bourne, Torrance, CA (US)

(73) Assignee: Alcon, Inc., Hunenberg (CH)

( * ) Notice: Subject to any disclaimer, the term of this patent is extended or adjusted under 35 U.S.C. 154(b) by 383 days.

(21) Appl. No.: 11/365,229

(22) Filed: Mar. 1, 2006

(65) Prior Publication Data

US 2007/0239102 A1    Oct. 11, 2007

(51) Int. Cl.
*A61M 25/16*    (2006.01)
*A61M 25/18*    (2006.01)
(52) U.S. Cl. ........................................................ 604/538
(58) Field of Classification Search .................. 604/104, 604/533, 538, 539
See application file for complete search history.

(56) References Cited

U.S. PATENT DOCUMENTS

| | | | |
|---|---|---|---|
| D45,165 S | 1/1914 | Warren | |
| 1,318,088 A | 10/1919 | Klein | |
| 1,507,362 A | 9/1924 | Bartosik | |
| 1,905,851 A | 4/1930 | Green | |
| 2,181,678 A | 11/1939 | Wright | |
| 2,249,906 A | 7/1941 | Longoria | |
| 2,598,060 A | 5/1952 | Kadesky | |
| 2,834,241 A | 5/1958 | Chowning | |
| 2,966,083 A | 12/1960 | Cheney | |
| 3,204,496 A | 9/1965 | Ingram | |
| 3,238,822 A | 3/1966 | Zuracki | |
| 3,398,612 A | 8/1968 | Batten | |
| 3,678,789 A | 7/1972 | Wilson | |
| 3,990,453 A | 11/1976 | Douvas et al. | |
| 4,329,892 A | 5/1982 | Daigle | |
| 4,526,067 A | 7/1985 | Gaquére | |
| 4,640,155 A | 2/1987 | Condon | |
| 4,710,176 A * | 12/1987 | Quick | 604/177 |
| 4,832,021 A | 5/1989 | Kuhl et al. | |
| 4,834,748 A | 5/1989 | McDonald | |
| 4,837,857 A | 6/1989 | Scheller et al. | |
| 4,858,504 A | 8/1989 | Tsai | |
| 4,884,478 A | 12/1989 | Lieser | |
| 4,908,015 A | 3/1990 | Anis | |
| 4,972,733 A | 11/1990 | Olmr et al. | |
| 4,979,355 A | 12/1990 | Ulevich | |
| 4,989,583 A | 2/1991 | Hood | |
| 5,057,119 A | 10/1991 | Clark et al. | |
| 5,059,210 A | 10/1991 | Clark et al. | |
| D321,461 S | 11/1991 | Hamilton | |
| 5,115,699 A | 5/1992 | Mertens | |

(Continued)

FOREIGN PATENT DOCUMENTS

EP    0455180 A1    11/1991

(Continued)

OTHER PUBLICATIONS

Advertisement for the Stealth Phaco Tip and Wrench (Hi-Line Medical), Fall 1992.

(Continued)

*Primary Examiner* — Theodore J Stigell
*Assistant Examiner* — Bradley J Osinski
(74) *Attorney, Agent, or Firm* — Darien Reddick

(57) ABSTRACT

A tip wrench/coupler having a generally hollow body for the storage and/or attachment of a tip, and a plurality of fluidic couplers that allow the wrench/coupler to connect two or more handpiece together in series, fluidically, thereby allowing the handpieces to be primed at the same time.

9 Claims, 5 Drawing Sheets

U.S. PATENT DOCUMENTS

| | | | |
|---|---|---|---|
| 5,133,726 A | 7/1992 | Ruiz et al. | |
| 5,162,044 A * | 11/1992 | Gahn et al. | 604/22 |
| 5,222,959 A | 6/1993 | Anis | |
| 5,224,400 A | 7/1993 | Maleski | |
| 5,261,922 A | 11/1993 | Hood | |
| D351,095 S | 10/1994 | Casica et al. | |
| D353,315 S | 12/1994 | Romeo | |
| D359,669 S | 6/1995 | Splingaire | |
| 5,511,451 A | 4/1996 | Steen et al. | |
| 5,620,427 A * | 4/1997 | Werschmidt et al. | 604/535 |
| 5,782,148 A | 7/1998 | Kerkhoven | |
| D422,474 S | 4/2000 | Shiao | |
| D425,770 S | 5/2000 | Hsieh | |
| D426,130 S | 6/2000 | Boukhny et al. | |
| D437,535 S | 2/2001 | Boukhny et al. | |
| 6,599,271 B1 * | 7/2003 | Easley | 604/119 |
| 2005/0277897 A1 | 12/2005 | Ghannoum et al. | |

FOREIGN PATENT DOCUMENTS

| | | |
|---|---|---|
| WO | WO 87/00788 A1 | 2/1987 |
| WO | WO 97/17902 A1 | 5/1997 |

OTHER PUBLICATIONS

Advertisement for Reusable Wrench (Myco Industries, Inc.), Fall 1994.

A. Chiron, PhacoTmesis™,Update: AAO, 1993, pp. 1-11.

Techni Tools Catalog, p. 66, Various Screwdriver bits, 1966.

* cited by examiner

COUPLER WRENCH

FIELD OF THE INVENTION

The present invention pertains to a wrench for the installation and removal of a tip onto and from a tool, and in particular, with respect to a tool for use in cataract surgery.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Surgical devices for performing such operations are typically hand-manipulatable and comprise a housing, a central shaft, and a cutting or polishing tip. A plurality of tips can be interchangeably mounted onto the distal end of the shaft. The tips each include a working end for performing the cutting or polishing and a mounting end having a threaded shank. The shank is screwed into a threaded bore formed in the end of the shaft. As can be appreciated, the tip must be securely attached to the shaft during the operation and the entire handpiece and all of its tubings must be primed. During a typical surgical procedure, more than one handpiece may be used, and this handpiece too must be primed. Priming of the handpiece(s) is a separate step, implemented following the attachment of any tip(s) with a tip wrench. Following tip attachment, prior art priming methods include placing a small rubber balloon or "test chamber" over the tip of the handpiece. Irrigation fluid is allowed to flow into the test chamber at the same time that fluid and air are aspirated out of the test chamber. In effect, the test chamber makes the irrigation/aspiration system a closed loop, much as when being used within an eye. The process is then repeated with any other handpieces that are going to be used in surgery. This process is time consuming and has the possibility for errors.

Accordingly, a need continues to exist for a device that assists in both the attachment of tips to and handpiece and the priming of the handpiece.

BRIEF DESCRIPTION OF THE INVENTION

The present invention improves upon the prior art by providing a tip wrench/coupler having a generally hollow body for the storage and/or attachment of a tip, and a plurality of fluidic couplers that allow the wrench/coupler to connect two or more handpiece together in series, fluidically, thereby allowing the handpieces to be primed at the same time.

Accordingly, one objective of the present invention is to provide a wrench for assisting in the attachment of surgical tips to surgical handpieces.

Another objective of the present invention is to provide a fluid coupling for surgical handpieces that allows two or more handpieces to be primed simultaneously.

Still another objective of the present invention is to provide a device for the storage of cutting tips to prevent damage prior to use.

These and other advantages and objectives of the present invention will become apparent from the detailed description and claims that follow.

DETAILED DESCRIPTION OF THE PREFERRED EMBODIMENTS

Figure 1:
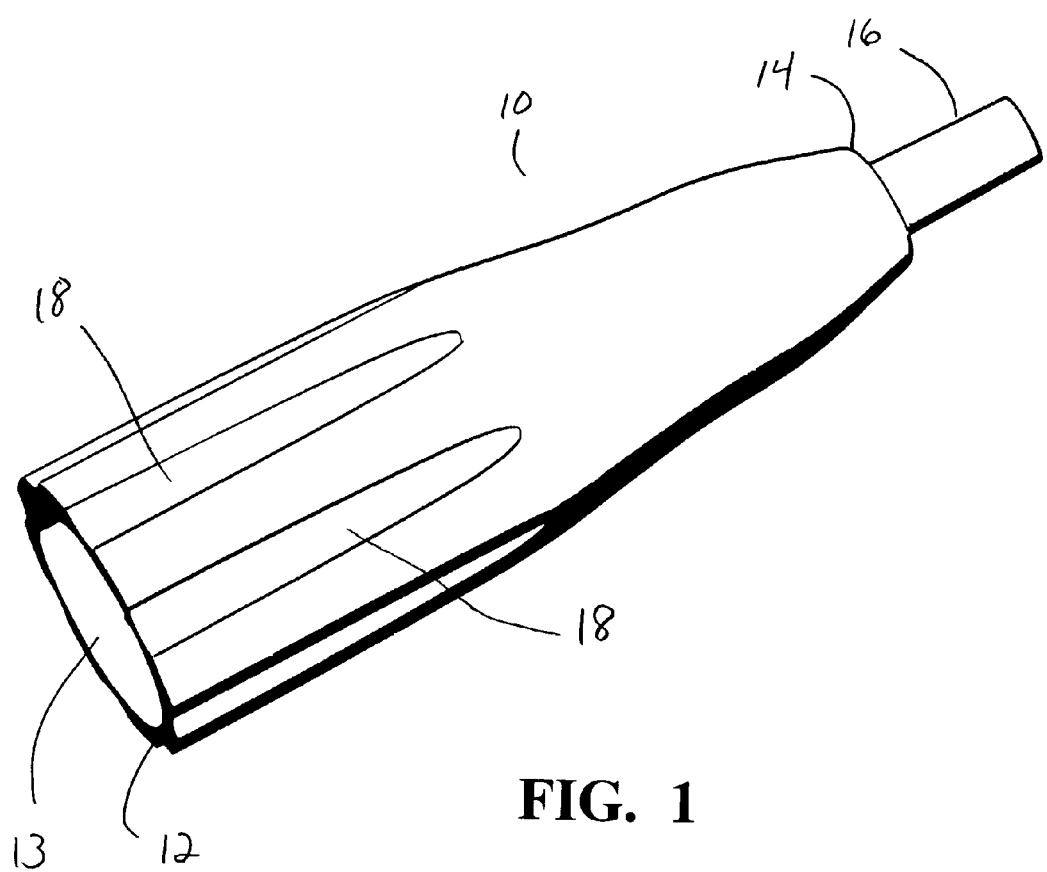
FIG. 1 is a perspective side view of the coupler/wrench of the present invention.
Figure 2:
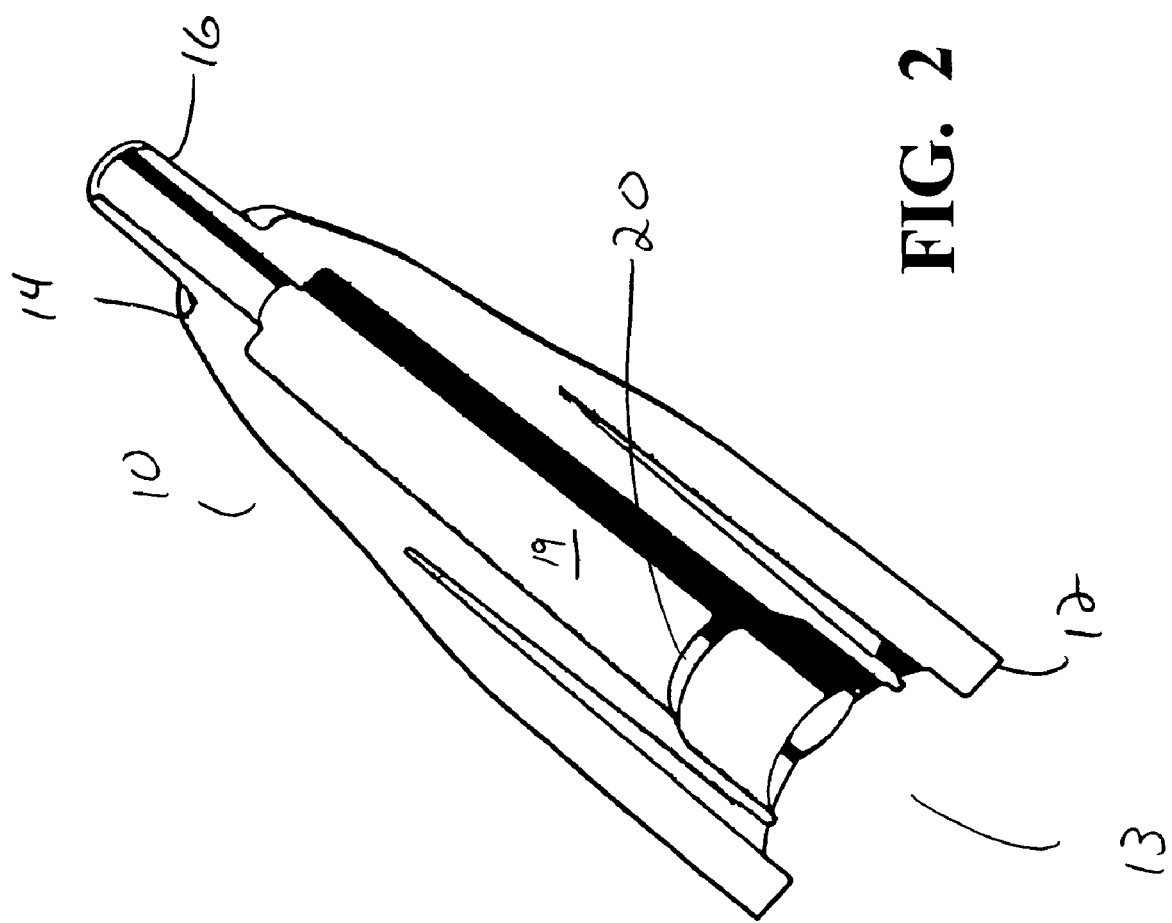
FIG. 2 is a partial cross-sectional view of the coupler/wrench of the present invention.
Figure 3:
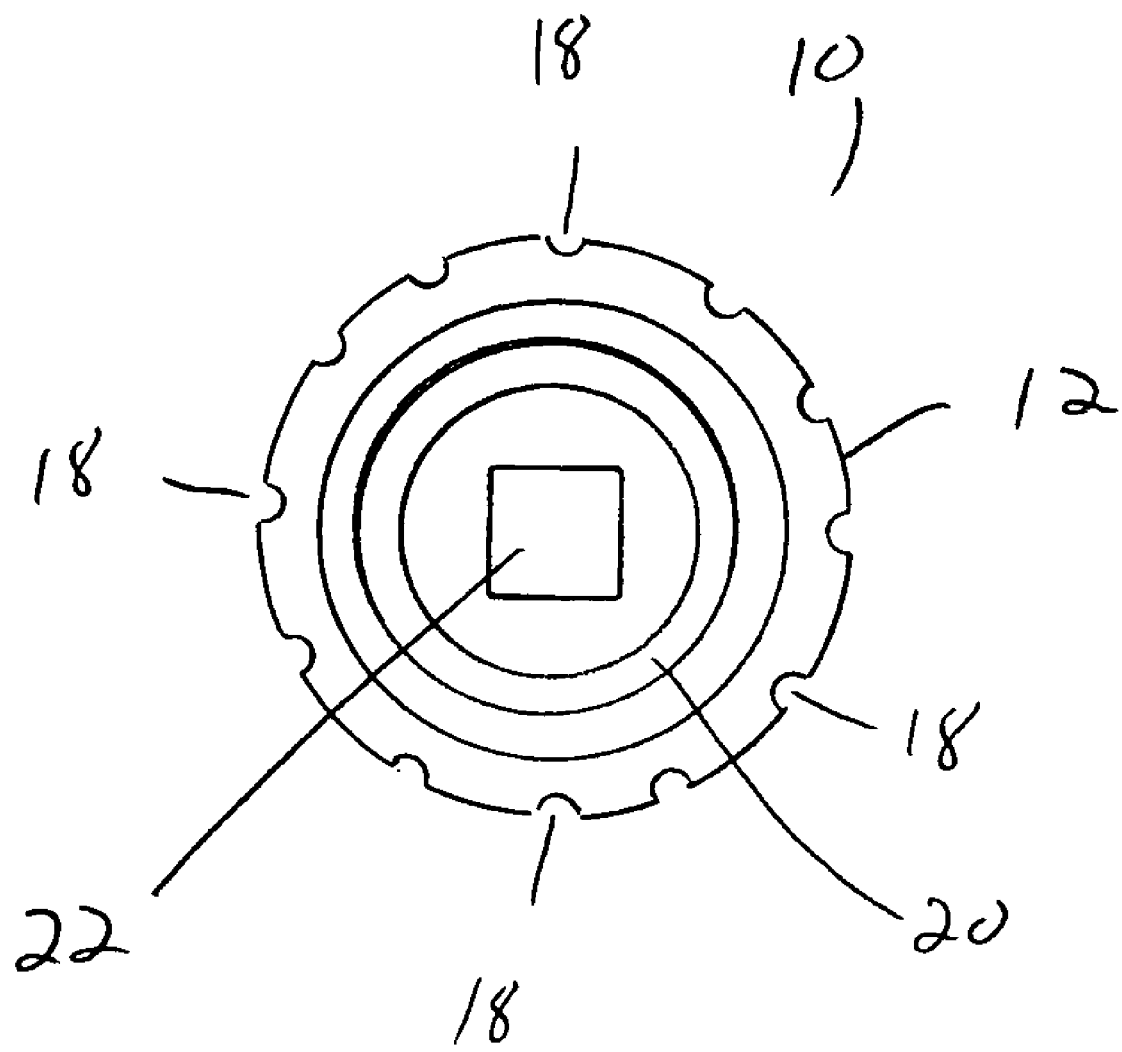
FIG. 3 is a proximal end elevational view of the coupler/wrench of the present invention.

As best seen in FIGS. 1 and 2, coupler wrench 10 of the present invention generally includes body 12 having open proximal end 13 and tapered distal end 14. Body 12 may contain a feature, such as knurling 18, for assisting in gripping coupler wrench 10. Body 12 is preferably made from a molded thermoplastic or other suitable material, such as stainless steel or titanium. Distal end 14 contains fitting 16, which may be a friction fluid coupler or a luer coupler. Proximal end 12 is generally open to bore 19. Bore 19 extends the entire length of coupler wrench 10 from opening 13 at proximal end 12 through fitting 16, thereby providing a fluid path from proximal end 12 through fitting 16. Bore 19 may be of varying diameters, for example, wider at proximal end 12 and narrower at fitting 16 with a tapered wall 20 containing a wrenching hole 22. Wrench hole 22 engages the hub of a phacoemulsification tip (not shown), thereby allowing the tightening of the tip onto handpiece 24. Alternatively, the phacoemulsification tip, or any other tip, can be held within coupler wrench 10 by friction or other means during storage or shipment.

Figure 4:
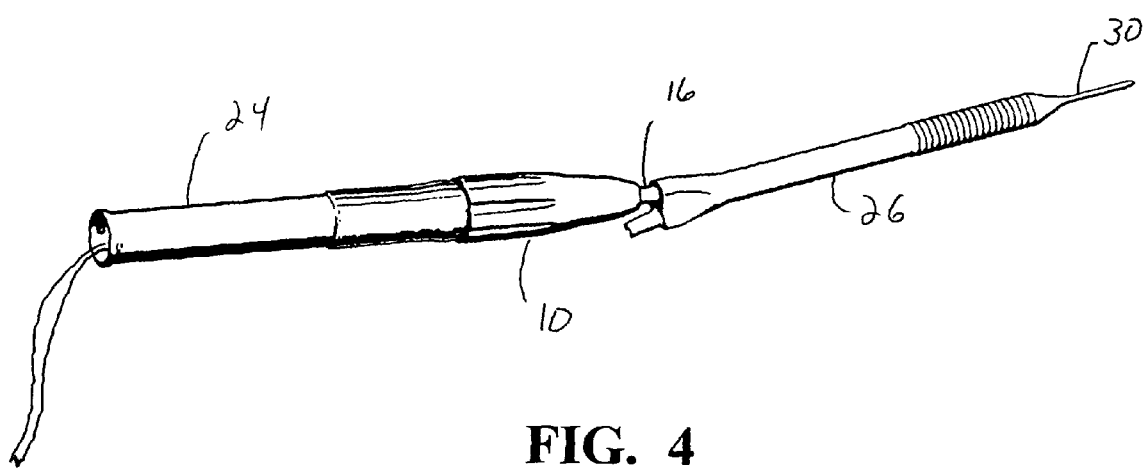
FIG. 4 is a perspective view illustrating one arrangement of coupling a phacoemulsification handpiece to an irrigation/aspiration handpiece using of the coupler/wrench of the present invention.
Figure 5:
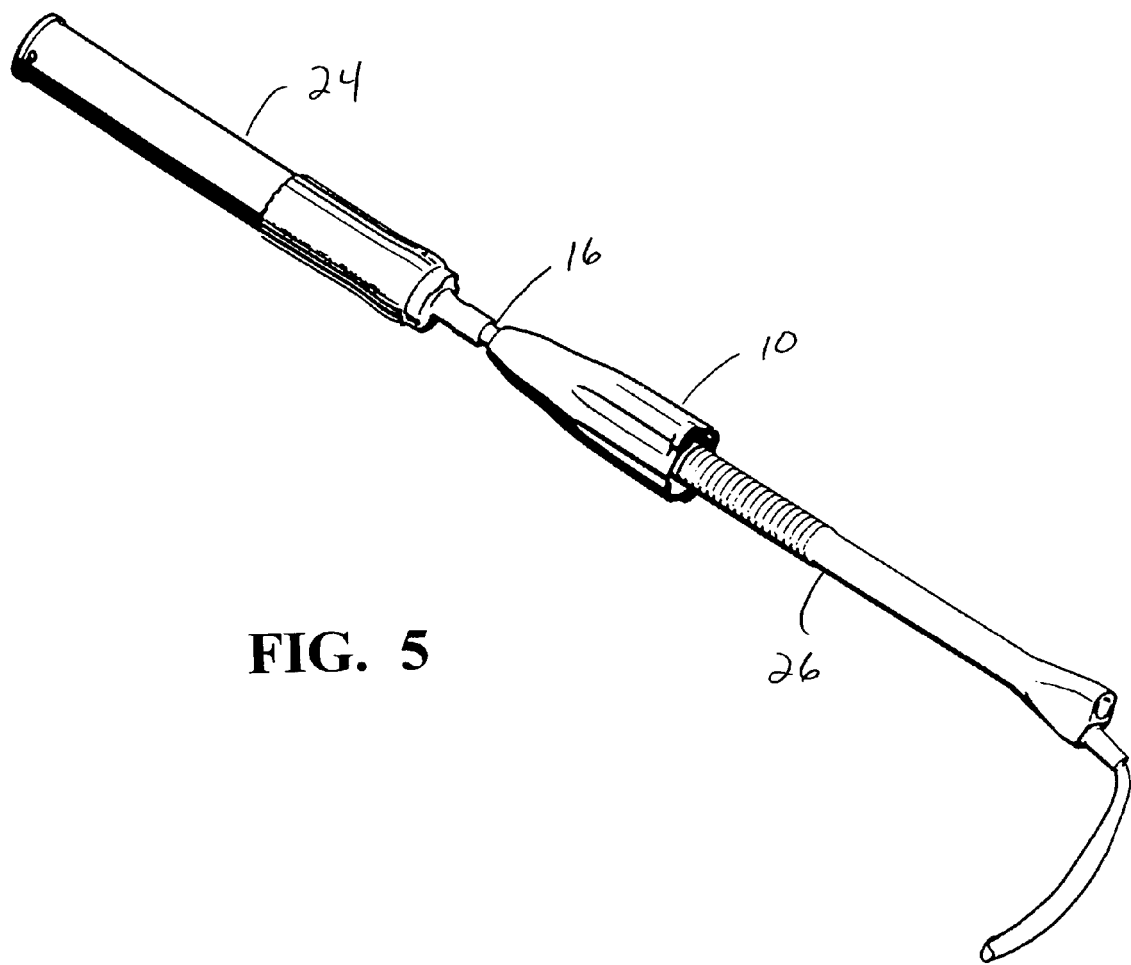
FIG. 5 is a perspective view illustrating an alternative arrangement of coupling a phacoemulsification handpiece to an irrigation/aspiration handpiece using of the coupler/wrench of the present invention.

As best seen in FIGS. 4 and 5, coupler wrench 10 may be attached to phacoemulsification handpiece 24 (FIG. 4) or irrigation/aspiration handpiece 26 (FIG. 5) so as to provide a fluid tight connection (for example, by use of a silicone rubber irrigation/aspiration sleeve 30, such sleeves being well-known in the art). Fitting 16 can be connect to irrigation aspiration handpiece 26 (FIG. 4) or phacoemulsification handpiece 24 (FIG. 5) so as to provide a continuous fluid path through phacoemulsification handpiece 24 and irrigation/aspiration handpiece 26. Such serial fluidic connection of handpieces 24 and 26 allow for simultaneous priming of both handpieces when pressurized irrigation fluid is supplied to the handpieces through fluid supply tube 40. One skilled in the art will recognize that other types of surgical tips may also be used with the present invention, for example, the tip described in U.S. Patent Publication No. 2005-0277897 (Ghannoum, et al.) and sold for use with the AQUALASE® surgical system may also be used.

This description is given for purposes of illustration and explanation. It will be apparent to those skilled in the relevant art that changes and modifications may be made to the invention described above without departing from its scope or spirit.

I claim:

1. A surgical system for simultaneous priming of a first handpiece and a second handpiece, comprising: a first surgical tool tip and a second surgical tool tip
   a first surgical handpiece having a first housing, a first passage, and a first distal end adapted to receive at least the first surgical tool tip;
   a second surgical handpiece having a second housing, a second passage, and a second distal end adapted to receive at least the second surgical tool tip; and
   a coupler wrench, the coupler wrench comprising:
      a) a body having a proximal end and a distal end;
      b) a fluid fitting attached to the distal end of the body;
      c) an opening at the proximal end of the body;
      d) a bore of varying diameter forming a fluid path between the opening and the fitting; and
      e) a wall in the bore, the wall having a wrenching hole, wherein the first surgical handpiece is attached to the coupler wrench at the proximal end and engages the wrench hole to form a fluid tight connection and the second surgical handpiece is connected to the fitting so as to provide a continuous fluid path through the first surgical handpiece and the second surgical handpiece.

2. The surgical system of claim 1 wherein the fitting is a friction fitting.

3. The surgical system of claim 1 wherein the fitting is a luer fitting.

4. The surgical system of claim 1, wherein the fluid tight connection comprises a silicone rubber irrigation/aspiration sleeve.

5. The surgical system of claim 1, wherein the body of the coupler wrench is formed from a molded thermoplastic, stainless steel, or titanium.

6. A surgical system for simultaneous priming of a first handpiece and a second handpiece, the surgical system comprising: a first surgical tool tip and a second surgical tool tip
   a first surgical handpiece comprising:
      a first housing;
      a first passage extending through the first housing; and
      a first distal end adapted to receive at least the first surgical tool tip;
   a second surgical handpiece comprising:
      a second housing;
      a second passage extending through the second housing; and
      a second distal end adapted to receive at least the second surgical tool tip; and
   a coupler wrench comprising:
      a body including a proximal end and a distal end;
      a fluid fitting attached to the distal end of the body;
      an opening at the proximal end of the body
      a bore of varying diameter forming a fluid path between the opening and the fitting;
      a wall in the bore; and
      a wrenching hole formed in the wall, the wrenching hole defined by at least one straight edge,
   wherein the first surgical handpiece is attached to the coupler wrench at the proximal end and engages the wrench hole to form a fluid tight connection and the second surgical handpiece is connected to the fitting so as to provide a continuous fluid path through the first surgical handpiece and the second surgical handpiece.

7. The surgical system of claim 6, wherein the wall in the bore of the coupler wrench is disposed transversely to the bore.

8. The surgical system of claim 6, wherein the wrenching hole is defined by a plurality of straight edges.

9. The surgical system of claim 8, wherein the plurality of straight edges forms a square opening.

* * * * *